(12) United States Patent
Ferris et al.

(10) Patent No.: US 11,439,489 B2
(45) Date of Patent: Sep. 13, 2022

(54) DENTAL MEDICAMENT APPLICATOR (71) Applicant: Cav-Aid LLC, Boerne, TX (US)

(72) Inventors: Tyler Ferris, Boerne, TX (US); Jeff Reeh, Boerne, TX (US)

(73) Assignee: Cav-Aid LLC, Boerne, TX (US)

(*) Notice: Subject to any disclaimer, the term of this patent is extended or adjusted under 35 U.S.C. 154(b) by 0 days.

(21) Appl. No.: 17/668,840

(22) Filed: Feb. 10, 2022

(65) Prior Publication Data
US 2022/0249217 A1    Aug. 11, 2022

Related U.S. Application Data (60) Provisional application No. 63/147,751, filed on Feb. 10, 2021.

(51) Int. Cl.
*A61C 19/06* (2006.01)
*A61K 9/00* (2006.01)

(52) U.S. Cl.
CPC .......... *A61C 19/063* (2013.01); *A61K 9/0063* (2013.01)

(58) Field of Classification Search
CPC .. A61K 9/22; A61C 19/06; A61C 5/80; A61C 15/00; A61C 15/04; A61C 8/00; A61C 19/063
USPC .............................. 433/80, 215, 216, 226, 229
See application file for complete search history.

(56) References Cited

U.S. PATENT DOCUMENTS

| | | | |
|---|---|---|---|
| 4,568,535 A * | 2/1986 | Loesche | A61K 9/0063 424/435 |
| 5,049,077 A * | 9/1991 | Goldin | A61C 19/06 433/80 |
| 5,087,200 A | 2/1992 | Brajnovic et al. | |
| 5,154,612 A | 10/1992 | Carlsson et al. | |
| 6,827,575 B1 | 12/2004 | Jorneus | |
| 7,056,118 B2 | 6/2006 | Allred et al. | |
| 7,118,376 B2 | 10/2006 | Jodaikin et al. | |
| D549,829 S | 8/2007 | Jodaikin et al. | |
| D553,245 S | 10/2007 | Jodaikin et al. | |
| 7,491,058 B2 | 2/2009 | Jorneus et al. | |
| D605,773 S | 12/2009 | Jodaikin et al. | |
| 7,850,453 B2 | 12/2010 | Jodaikin et al. | |
| 7,883,336 B2 | 2/2011 | Hansson | |
| 8,287,277 B2 | 10/2012 | Jodaikin et al. | |
| 9,668,844 B2 | 6/2017 | Jodaikin et al. | |
| 10,849,729 B2 | 12/2020 | Sagel et al. | |
| 2005/0175959 A1 | 8/2005 | Jodaikin et al. | |
| 2005/0196727 A1* | 9/2005 | Jessop | A61C 19/06 433/229 |
| 2005/0239015 A1 | 10/2005 | Dragan | |
| 2015/0125810 A1* | 5/2015 | Jodaikin | A61C 19/063 433/80 |
| 2015/0290122 A1* | 10/2015 | Boe | A61C 19/063 424/435 |
| 2021/0000579 A1 | 1/2021 | Higdon | |

FOREIGN PATENT DOCUMENTS

| | | |
|---|---|---|
| DE | 202009009789 | 10/2009 |
| EP | 1263347 | 5/2007 |
| WO | WO2017182425 | 10/2017 |

OTHER PUBLICATIONS

Chong et al., "Slow-release fluoride devices for the control of dental decay (Review)." Cochrane Database of Systematic Reviews 2018, Issue 3, (Year: 2018).*
Shutz Dental Micerium Group, IMPLA Interim Implant, Impla temp.implant, 3,3/11,5mm, 10pcs, The Interim Implant, for securely fixing drilling templates and temporary bridges, date accessed Jul. 7, 2011, 1 page, Rosbach, Germany.
WIPO International Search Report and Written Opinion of the International Searching Authority for PCT/US2022/016006 dated May 6, 2022.

* cited by examiner

*Primary Examiner* — Walter E Webb
(74) *Attorney, Agent, or Firm* — Scott Griggs; Griggs Bergen LLP (57) ABSTRACT

A dental medicament applicator is disclosed. In one embodiment, a retention device is sized for insertion at a dental site, such as an interproximal site. The retention device includes a body and at least one matrix within the body containing a topical substance, such as a fluoride-containing chemical agent, silver diamine fluoride, or a peptide-based chemical agent, for example. One or two wings may be selectively separably coupled to respective ends of the body. The body, in response to being physically affixed to the dental site, delivers the topical substance at a controlled rate to the dental site.

20 Claims, 8 Drawing Sheets

DENTAL MEDICAMENT APPLICATOR

PRIORITY STATEMENT & CROSS-REFERENCE TO RELATED APPLICATIONS

This application claims priority from U.S. Patent Application No. 63/147,751, entitled "Dental Medicament Applicator" and filed on Feb. 10, 2021, in the name of Tyler Ferris et al.; which is hereby incorporated by reference, in entirety, for all purposes.

TECHNICAL FIELD OF THE INVENTION

The present disclosure relates, in general, to dental devices for treatment and care of the teeth in an oral cavity, and more particularly, to a dental medicament applicator for treating interproximal caries and the like.

BACKGROUND OF THE INVENTION

Dental caries, which are also referred to as tooth decay or cavities, are one of the most common and widespread persistent diseases in the oral cavity. When an individual eats certain food, bacteria in the oral cavity break down the food and produce acids that have the ability to seriously damage hard tissues of a tooth in the oral cavity. The result may be the formation of dental caries. In current clinical dentistry practice, interproximal caries are extremely difficult to treat due to the location of the dental caries between teeth. Accordingly, there is a need for improved systems and methods for effectively treating dental caries and, in particular, hard to reach interproximal caries.

SUMMARY OF THE INVENTION

It would be advantageous to achieve systems and methods that would improve upon existing limitations in functionality with respect to treatment of dental caries and, in particular, interproximal caries. It would also be desirable to enable a mechanical-based and chemical-based medical solution that would provide simplified and accelerated treatment of interproximal caries. To better address one or more of these concerns, a dental medicament applicator is disclosed. In one embodiment of the dental medicament applicator, a retention device is sized for insertion at a dental site, such as an interproximal site. The retention device includes a body and at least one matrix within the body containing a topical substance, such as a fluoride-containing chemical agent, silver diamine fluoride, or a peptide-based chemical agent, for example. One or two wings may be selectively separably coupled to respective ends of the body. The body, in response to being physically affixed to the dental site, delivers the topical substance at a controlled rate to the dental site. These and other aspects of the invention will be apparent from and elucidated with reference to the embodiments described hereinafter.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which.

DETAILED DESCRIPTION OF THE INVENTION

While the making and using of various embodiments of the present invention are discussed in detail below, it should be appreciated that the present invention provides many applicable inventive concepts, which can be embodied in a wide variety of specific contexts. The specific embodiments discussed herein are merely illustrative of specific ways to make and use the invention, and do not delimit the scope of the present invention.

Referring initially to FIG. 1 through FIG. 8D, therein is depicted one embodiment of a dental medicament applicator that may be utilized to treat dental caries and interproximal caries, for example, which is schematically illustrated and designated 10. A retention device 12 is sized for insertion at a dental site, such as an interproximal site. As shown, the retention device 12 includes a body 14 having a front 16, a rear 18, an upper end 20, a lower end 22, a lateral end 24, and a lateral end 26. The body 14 also includes a vertical axis 28 and a horizontal axis 30.

A wing 40 includes a front 42, a rear 44, an upper end 46, a lower end 48, a proximal end 50, and a distal end 52. The wing 40 has the shape of a lobe 54. Also, the wing 40 has a hole 56 therethrough proximate the distal end 52. The hole 56 may be sized to accept a soft thread or dental floss, for example. The proximal end 50 of the wing 40 is selectively separably coupled to the lateral end 24 by three points of contact 58, 60, 62. As shown, the three points of contact 58, 60, 62 define two windows 64, 66. Each of the two windows 64, 66 provides a respective line-of-sight opening 68, 70 through the retention device 12. It should be appreciated that although the lateral end 24 of the body 14 is selectively separably coupled by the three points of contact 58, 60, 62 defining the two windows 64, 66, the number of points of contact and associated windows may vary depending on the application. As will be discussed in further detail hereinbelow, the line-of-sight openings 68, 70 provide a visual indicator to assist in the placement of the dental medicament applicator 10.

A wing 80 includes a front 82, a rear 84, an upper end 86, a lower end 88, a proximal end 90, and a distal end 92. The wing 80 also has the shape of a lobe 94. Moreover, the wing 80 has a hole 96 therethrough proximate the distal end 92. The hole 96 may be sized to accept a soft thread or dental floss, for example. The proximal end 90 of the wing 80 is selectively separably coupled to the lateral end 26 by three points of contact 98, 100, 102. As shown, the three points of contact 98, 100, 102 define two windows 104, 106. Each of the two windows 104, 106 provides a respective line-of-sight opening 108, 100 through the retention device 12.

Figures 1, 5, 6:
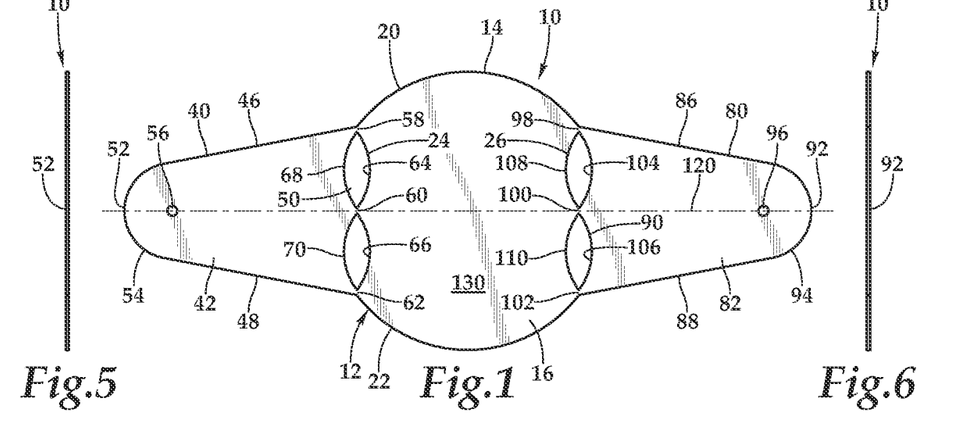
FIG. 1 is a front elevation view of one embodiment of a dental medicament applicator, according to some exemplary aspects of the teachings presented herein.
FIG. 5 is a lateral elevation view of the dental medicament applicator depicted in FIG. 1.
FIG. 6 is another lateral elevation view of the dental medicament applicator depicted in FIG. 1.
Figure 2:
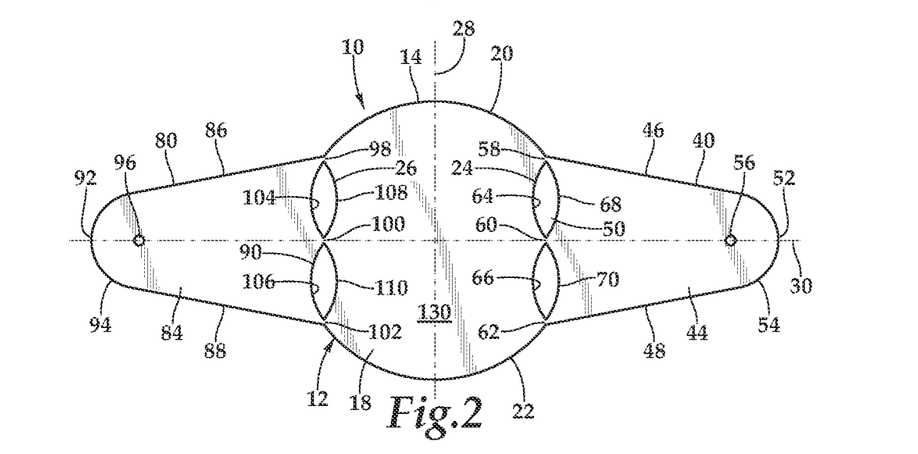
FIG. 2 is a rear elevation view of the dental medicament applicator depicted in FIG. 1.
Figure 3:
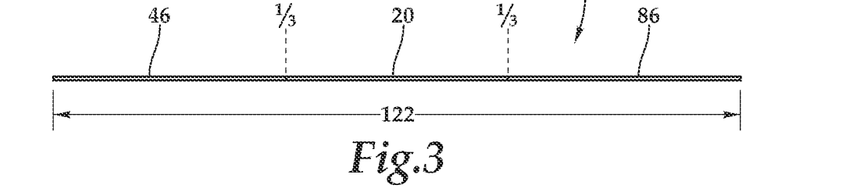
FIG. 3 is a top plan view of the dental medicament applicator depicted in FIG. 1.
Figure 4:
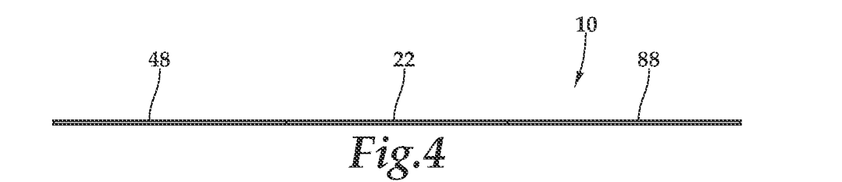
FIG. 4 is a bottom plan view of the dental medicament applicator depicted in FIG. 1.

As shown in the illustrated embodiment, the retention device 12 of the dental medicament applicator 10 may include a transverse axis 120 from the distal end 52 of the wing 40 through the body 14 to the distal end 92 of the wing 80. The transverse axis 120 has a transverse length 122. The body 14 may extend along the transverse axis 120 and intersect the transverse length 122 from one-third (⅓) of the transverse length 122 measured from the distal end 52 of the wing 40 to one-third (⅓) of the transverse length 122 measured from the distal end 92 of the wing 80. Furthermore, in some embodiments, the surface area of the body 14 may be greater than the surface area of each of the wings 40, 80. In some embodiments, the surface area of the body 14 is less than the surface area of the wing 40 plus the surface area of the wing 80. In some other embodiments, the surface area of the body 14 is greater than the surface area of the wing 40 plus the surface area of the wing 80. Further, as will be appreciated and discussed in additional detail hereinbelow, each of the wings 40, 80 may include a shape such as, for example, single lobes, double lobes, polygon forms, and rectangular forms.

At least one matrix 130 within the body contains a topical substance. The matrix 130 may include biodegradable materials, bioresorbable materials, or resorbable materials, for example. The matrix 130 may be a polymeric membrane or disc. By way of example and not by way of limitation, the matrix 130 may comprise a synthetic polymer or a natural polymer which may be at least one of polysacaccharides, lipids, polyisoprene, gum and proteins, or any mixture thereof. The natural polymer may be a protein selected from collagen and gelatin, for example. Preferably, the polymer is cross-linked, typically by at least one of glutaraldehyde, formaldehyde, glycol dimethacrylate, tannic acid, and allyl methacrylate.

The matrix 130 may also include, by way of example, and not by way of limitation, a starch-based polymer selected from the group consisting of native starches, modified Starches, and thermoplastic starch polymers. The matrix may also include, by way of further example, and not by way of limitation, at least one synthetic polymer selected from the group consisting of polyvinyl alcohols, polyester amides, polyester urethanes, aliphatic polyesters, aromatic polyesters, and copolymers of aliphatic polyesters and aromatic polyesters. The matrix 130 may optionally further include an auxiliary agent which may be any one of an enhancing agent for enhancing the release of the active material, plasticizing, elasticizing, coloring and staining, filling and softening, and preserving, for example. The body 14 and the wings 40, 80 may have a similar composition to the matrix 130.

The body 14, in response to being physically affixed to the dental site, delivers the topical substance at a controlled rate to the dental site. The topical substance may be a fluoride-containing chemical agent. By way of example, and not by way of limitation, the topical substance may be any one of inorganic or organic fluoride-containing chemical agents, including sodium fluoride, Stannous fluoride, Stannous hexafluorozirconate, calcium fluoride, difluorosilane, hydrogen fluoride, sodium monofluorophosphate, ytterbium trifluoride, sodium hexafluorosilicate, ammonium fluoride, amine fluoride, and fluoroaluminosilicate glass, as well as any mixture thereof. The period of fluoridation required by the chemical agent is dependent on the type of fluoride, concentration, and period of delivery. It should be appreciated that other chemical or physical interventions and the type of surface or lesion being treated may also impact the period of fluoridation. Further, chronic toxicity due to fluoride (F) may be reached at 0.1 mg F/Kg of body weight. Thus, the weight of the patient impacts fluoride concentration as well. By way of example, and not by way of limitation, in applications where sodium fluoride is selected, the applicable concentration will be 1%-4%.

In another implementation, the topical substance may be silver diamine fluoride. Silver diamine fluoride (SDF), a clear liquid that combines the antibacterial effects of silver and the remineralizing effects of fluoride, is a promising therapeutic agent for managing caries lesions in young children and those with special care needs. SDF has only recently become available in the United States. SDF may also have the name "silver-diamine fluoride" or "silver diamine fluoride" or "silver hydrazine fluoride." SDF is frequently utilized as an aqueous SDF, 34% to 42% weight/volume, with 38% weight volume being preferred in many cases, with a presentation as a light-sensitive liquid with ammonia odor and blue coloring having a specific gravity of about 1.25. When the silver in SDF is applied to a dental site on a tooth, it oxidizes and leaves a black stain on the damaged cavity portion of the tooth and may cause staining in other areas of the oral cavity. Therefore, SDF must be delivered at a controlled rate to the desired dental site. The dental medicament applicator 10 accomplishes this goal as will be discussed in further detail hereinbelow.

As mentioned, the body 14, in response to being physically affixed to the dental site, delivers the topical substance at a controlled rate to the dental site. The topical substance may be a peptide-based chemical agent. The peptide-based chemical agent may include, by way of example and not by way of limitation, polypeptides, or the composition may further comprise one or more other active agents suitable for an intended use, including but not limited to anti-microbial polypeptides (inhibiting bacterial infection), biomineralization-promoting polypeptides (i.e., any polypeptides that are useful for controlling or promoting biomineralization), inorganic material-binding polypeptides, three-dimensional scaffold-forming polypeptides, collagen, chitosan, amphiphilic peptides, protein-binding polypeptides, enamelin-derived polypeptides, tuftelin-derived peptides, statherin-derived polypeptides, dentin-derived polypeptides, bone sialoprotein-derived polypeptides, osteocalcin-derived polypeptides, osteopontin-derived polypeptides, proteins with caries inhibitory activity, casein, and bone morphogenetic-derived polypeptides.

By way of further example, and not by way of limitation, the topical substance, when including the peptide-based chemical agent, may be a combination of amelogenin, an inorganic or organic fluoride-containing chemical agent, an inorganic or organic calcium-containing chemical agent, and an inorganic or organic phosphate-containing chemical agent. By way of further example, and not by way of limitation, the topical substance may be at least one of amelogenin, an inorganic or organic fluoride-containing chemical agent, an inorganic or organic calcium-containing chemical agent, and an inorganic or organic phosphate-containing chemical agent.

Amelogenins are a group of protein isoforms produced by alternative splicing or proteolysis from the AMELX gene, on the X chromosome, and also the AMELY gene in males, on the Y chromosome. Amelogenins are involved in amelogenesis, the development of enamel. Amelogenins are type of extracellular matrix protein, which, together with ameloblastins, enamelins and tuftelins, direct the mineralization of enamel to form a highly organized matrix of rods, interrod crystal and proteins. As previously discussed, the inorganic or organic fluoride-containing chemical agent may be sodium fluoride, Stannous fluoride, Stannous hexafluorozirconate, calcium fluoride, difluorosilane, hydrogen fluoride, sodium monofluorophosphate, ytterbium trifluoride, sodium hexafluorosilicate, ammonium fluoride, amine fluoride, and fluoroaluminosilicate glass, as well as any mixture thereof.

By way of example, and not by way of limitation, the inorganic or organic calcium-containing chemical agent may be integrated into calcium phosphates, casein phosphopeptide/amorphous calcium phosphate nanocomplexes, casein phosphopeptide-amorphous calcium phosphate, octacalcium phosphate complexes, calcium phosphate crystal structures, dicalcium phosphate dihydrate-based compounds, calcium phosphate pastes, or in vitro calcium phosphate mineralizable compounds. Also, by way of example and not by way of limitation, the inorganic or organic phosphate-containing chemical agent may be integrated into calcium phosphates, casein phosphopeptide/amorphous calcium phosphate nanocomplexes, casein phosphopeptide-amorphous calcium phosphate, octacalcium phosphate complexes, calcium phosphate crystal structures, dicalcium phosphate dihydrate-based compounds, calcium phosphate pastes, or in vitro calcium phosphate mineralizable compounds.

Figure 7:
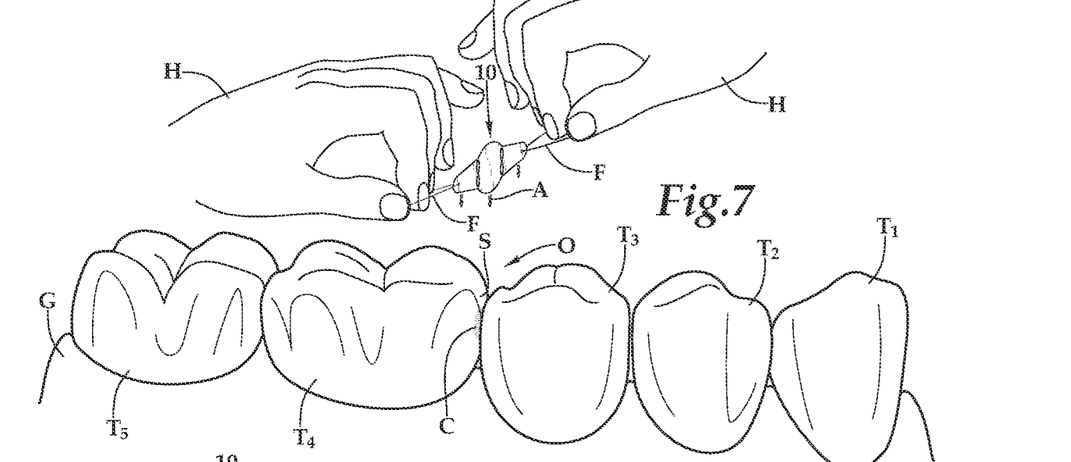
FIG. 7 is an illustrative diagram depicting a lingual view from a tongue of an oral cavity where the dental medicament applicator of FIG. 1 is being utilized, according to some exemplary aspects of the teachings presented herein.
Figures 8A, 8B, 8C, 8D:
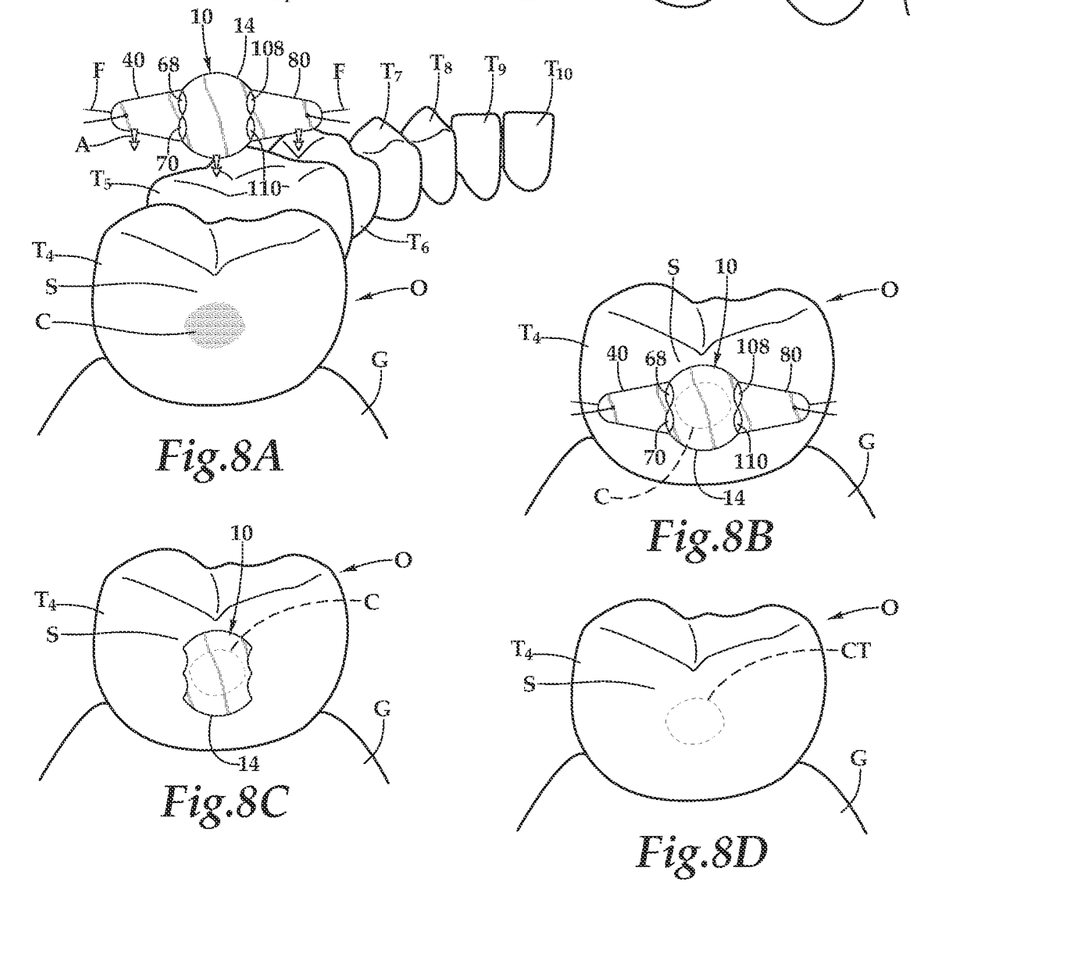
FIG. 8A is an illustrative diagram depicting a cross-sectional view of an interproximal space between two teeth where the dental medicament applicator of FIG. 1 is in a first operational configuration.
FIG. 8B is an illustrative diagram depicting a cross-sectional view of an interproximal space between two teeth where the dental medicament applicator of FIG. 1 is in a second operational configuration.
FIG. 8C is an illustrative diagram depicting a cross-sectional view of an interproximal space between two teeth where the dental medicament applicator of FIG. 1 is in a third operational configuration.
FIG. 8D is an illustrative diagram depicting a cross-sectional view of an interproximal space between two teeth where the dental medicament applicator of FIG. 1 is in a fourth operational configuration.

Referring now to FIG. 7 through FIG. 8D, in one operational embodiment, the dental medicament applicator 10 is being utilized within an oral cavity O having teeth $T_1$, $T_2$, $T_3$, $T_4$, $T_5$, $T_6$, $T_7$, $T_8$, $T_9$, and $T_{10}$ as well as gum tissue G. Dental caries C, which represent the dental site, are located on an interproximal surface S of tooth $T_4$. A dental professional having hands H is positioning the dental medicament applicator 10 with the use of dental floss F in a direction of placement A between teeth $T_3$ and $T_4$. As best seen in FIG. 8A and FIG. 8B, the dental professional positions the body 14 of the dental medicament applicator 10 over the dental caries C. As shown, the line-of-sight openings 68, 70, 108, 110 are utilized to correctly position the body 14 of the dental medicament applicator 10 such that the wings 40, 80 are adjacent to the dental caries C. As best seen in FIG. 8B and FIG. 8C, once the body 14 of the dental medicament applicator 10 is correctly positioned and affixed to the dental site, the dental professional selectively separates each of the wings 40, 80 from the body 14. As best seen in FIG. 8C and FIG. 8D, the body 14, in response to being physically affixed to the dental site, delivers the topical substance at a controlled rate to the dental caries C. The body 14 is then bio-reabsorbed leaving a treated dental caries CT, which is best seen in FIG. 8D. In this manner the dental medicament applicator 10 provides simplified and accelerated treatment of interproximal caries that is targeted to a specific dental site, thereby mitigating the risk of undesired contact between the topical substance and other bone or tissue.

Figure 9:
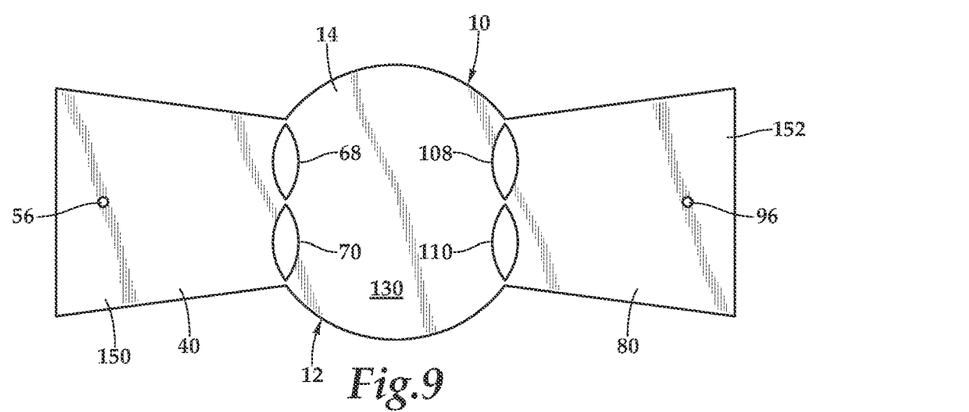
FIG. 9 is a front elevation view of a further embodiment of a dental medicament applicator.
Figure 10:
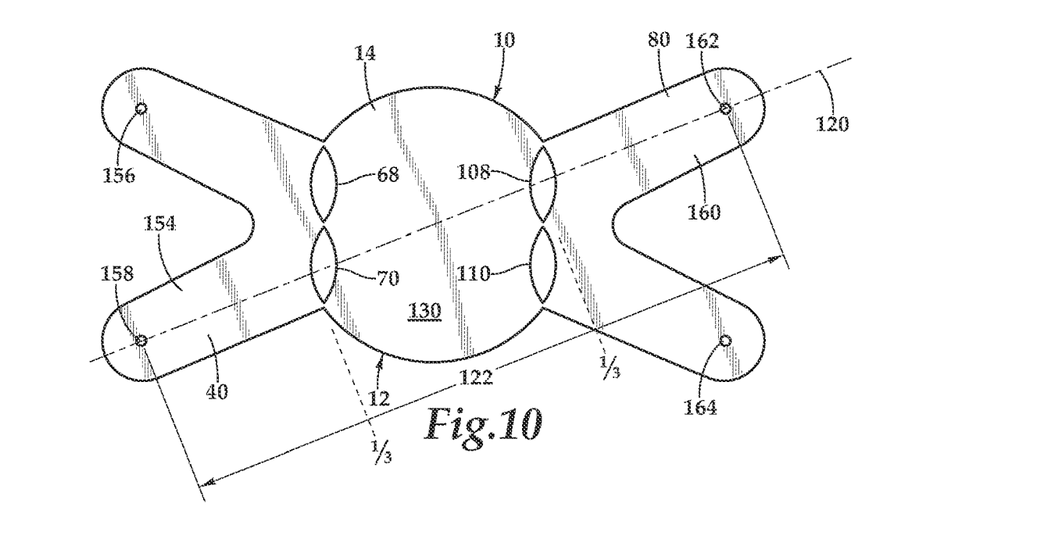
FIG. 10 is a front elevation view of a still further embodiment of a dental medicament applicator.
Figure 11:
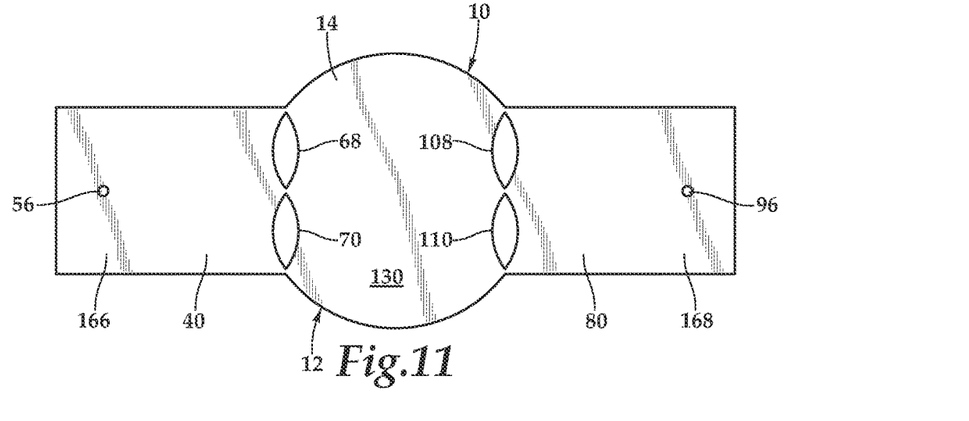
FIG. 11 is a front elevation view of an additional embodiment of a dental medicament applicator.

Other embodiments of the dental medicament applicator will now be presented in FIG. 9 through FIG. 34. Referring initially to FIG. 9, the dental medicament applicator 10 includes the body 14 with the wings 40, 80. The wing 40 has a polygon form 150, which is shown as an isosceles trapezium. Similarly, the wing 80 has a polygon form 152, which is also shown as an isosceles trapezium. Referring now to FIG. 10, the dental medicament applicator 10 includes the body 14 with the wings 40, 80. The wing 40 has a double lobe form 154, which supports holes 156, 158. Similarly, the wing 80 has a double lobe form 160, which supports holes 162, 164. Referring now to FIG. 11, the dental medicament applicator 10 includes the body 14 with the wings 40, 80. The wing 40 has a rectangular form 166. Similarly, the wing 80 has a rectangular form 168.

Referring now to FIG. 12 through FIG. 17, in some embodiments of the dental medicament applicator 10, a retention device 182 is sized for insertion at a dental site, such as an interproximal site. As shown, the retention device 182 includes a body 184 having a front 186, a rear 188, an upper end 190, a lower end 192, a lateral end 194, and a lateral end 196. The body 184 also includes a vertical axis 198 and a horizontal axis 200.

A wing 210 includes a front 212, a rear 214, an upper end 216, a lower end 218, a proximal end 230, and a distal end 232. The wing 210 has the shape of a lobe 234. Also, the wing 210 has a hole 236 therethrough proximate the distal end 232. The hole 236 may be sized to accept a soft thread or dental floss, for example. The proximal end 230 of the wing 210 is selectively separably coupled to the lateral end 194 by three points of contact 238, 240, 242. As shown, the three points of contact 238, 240, 242 define two windows 244, 246. Each of the two windows 224, 246 provides a respective line-of-sight opening 248, 250 through the retention device 12. As previously discussed, the line-of-sight openings 248, 250 provide a visual indicator to assist in the placement of the dental medicament applicator 10.

Figure 12:
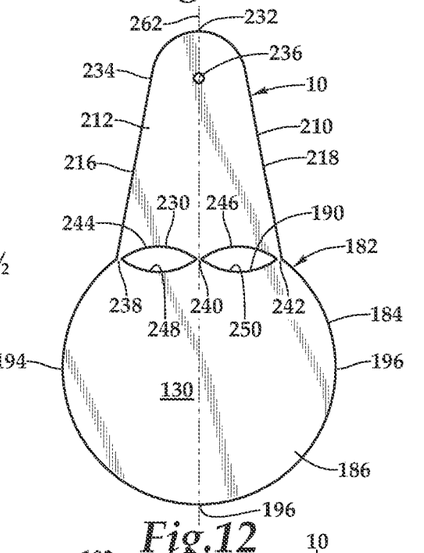
FIG. 12 is a front elevation view of another embodiment of a dental medicament applicator.
Figure 13:
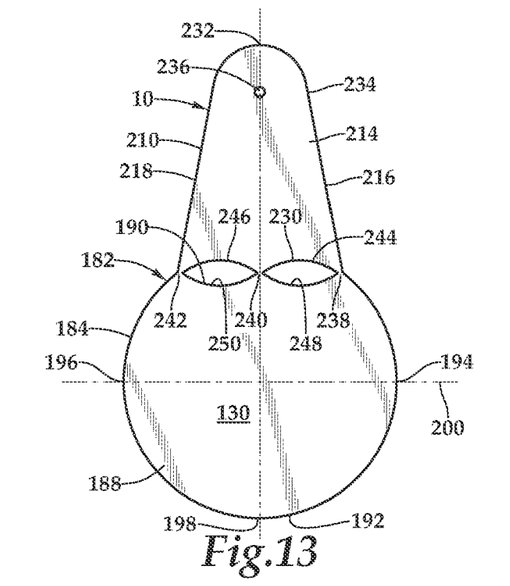
FIG. 13 is a rear elevation view of the dental medicament applicator depicted in FIG. 12.
Figure 14:
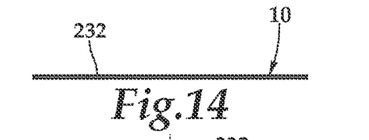
FIG. 14 is a top plan view of the dental medicament applicator depicted in FIG. 12.
Figure 15:
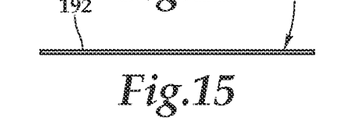
FIG. 15 is a bottom plan view of the dental medicament applicator depicted in FIG. 12.
Figure 16:
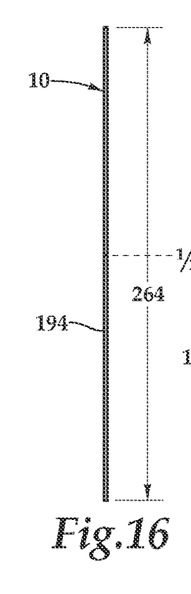
FIG. 16 is a lateral elevation view of the dental medicament applicator depicted in FIG. 12.
Figure 17:
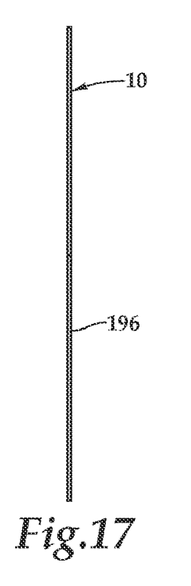
FIG. 17 is another lateral elevation view of the dental medicament applicator depicted in FIG. 12.

In the illustrated embodiment, the retention device 182 includes a transverse axis 262 from the distal end 232 of the wing 210 through the body 184. The transverse axis 262 includes a transverse length 264. The body 184 may extend along the transverse axis 262 and intersect the transverse length 264 from the lateral end 196 to one-half (½) of the transverse length 264 measured from the distal end 232 of the wing 210. Also, in some embodiments, the surface area of the body 184 may be greater than the surface area of the wing 210. Alternatively, the surface area of the body 184 may be greater than twice the surface area of the wing 210.

Referring now to FIG. 18 through FIG. 23, the dental medicament applicator 10 includes a retention device 312 that is sized for insertion at a dental site, such as an interproximal site. As shown, the retention device 312 includes a body 314 having a front 316, a rear 318, an upper end 320, a lower end 322, a lateral end 324, and a lateral end 326. The body 314 also includes a vertical axis 328 and a horizontal axis 330.

A wing 340 includes a front 342, a rear 344, an upper end 346, a lower end 348, a proximal end 350, and a distal end 352. The wing 340 has the shape of a lobe 354. Also, the wing 340 has a hole 356 therethrough proximate the distal end 352. The hole 356 may be sized to accept a soft thread or dental floss, for example. The proximal end 350 of the wing 340 is selectively separably coupled to the lateral end 324 by a perforation 360, which provides a visual indicator 362 to assist in the placement of the dental medicament applicator 10.

A wing 380 includes a front 382, a rear 384, an upper end 386, a lower end 388, a proximal end 390, and a distal end 392. The wing 380 also has the shape of a lobe 394. Moreover, the wing 380 has a hole 396 therethrough proximate the distal end 392. The hole 396 may be sized to accept a soft thread or dental floss, for example. The proximal end 390 of the wing 380 is selectively separably coupled to the lateral end 326 by a perforation 400, which provides a visual indicator 402 to assist in the placement of the dental medicament applicator 10.

Figures 18, 22, 23:
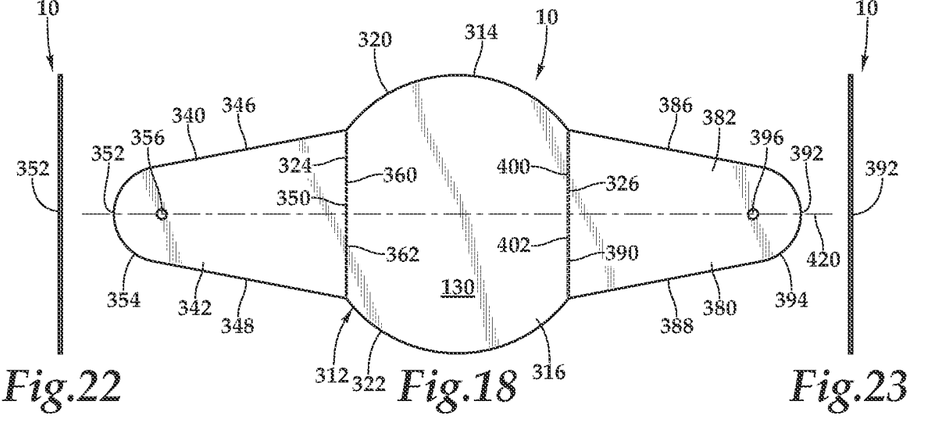
FIG. 18 is a front elevation view a further dental medicament applicator, according to some exemplary aspects of the teachings presented herein.
FIG. 22 is a lateral elevation view of the dental medicament applicator depicted in FIG. 18.
FIG. 23 is another lateral elevation view of the dental medicament applicator depicted in FIG. 18.
Figure 19:
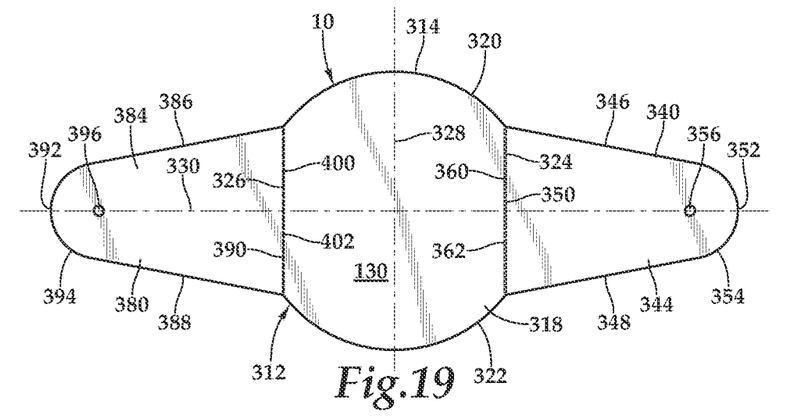
FIG. 19 is a rear elevation view of the dental medicament applicator depicted in FIG. 18.
Figure 20:
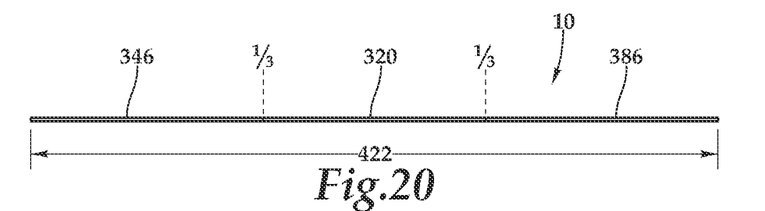
FIG. 20 is a top plan view of the dental medicament applicator depicted in FIG. 18.
Figure 21:
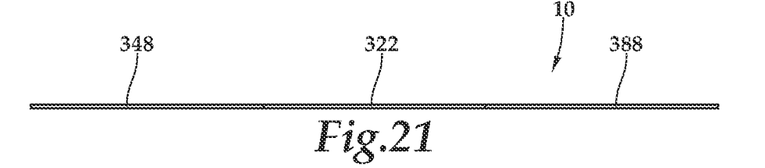
FIG. 21 is a bottom plan view of the dental medicament applicator depicted in FIG. 18.

As shown in the illustrated embodiment, the retention device 312 of the dental medicament applicator may include a transverse axis 420 from the distal end 352 of the wing 340 through the body 314 to the distal end 392 of the wing 380. The transverse axis 420 has a transverse length 422. The body 314 may extend along the transverse axis 420 and intersect the transverse length 422 from one-third (⅓) of the transverse length 422 measured from the distal end 352 of the wing 340 to one-third (⅓) of the transverse length 422 measured from the distal end 392 of the wing 380. Furthermore, in some embodiments, the surface area of the body 314 may be greater than the surface area of each of the wings 340, 380. In some embodiments, the surface area of the body 314 is less than the surface area of the wing 340 plus the surface area of the wing 380. In some other embodiments, the surface area of the body 314 is greater than the surface area of the wing 340 plus the surface area of the wing 380. Further, as will be appreciated and discussed in additional detail hereinbelow, each of the wings 340, 380 may include a shape such as for example, single lobes, double lobes, polygon forms, and rectangular forms. The matrix 130 within the body 314 contains the topical substance. The body 314 and the wings 340, 380 may have a similar composition to the matrix 130. The body 314, in response to being physically affixed to the dental site, delivers the topical substance at a controlled rate to the dental site.

Figure 24:
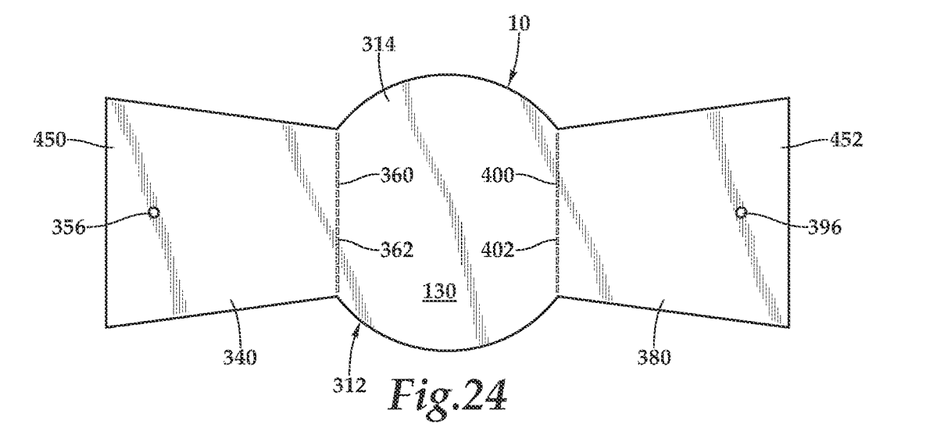
FIG. 24 is a front elevation view of a further embodiment of a dental medicament applicator.
Figure 25:
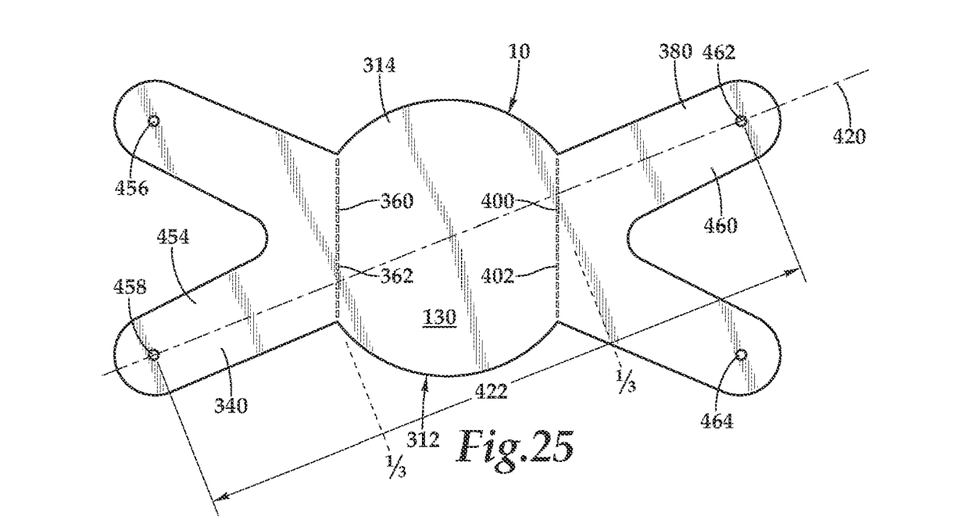
FIG. 25 is a front elevation view of a still further embodiment of a dental medicament applicator.
Figure 26:
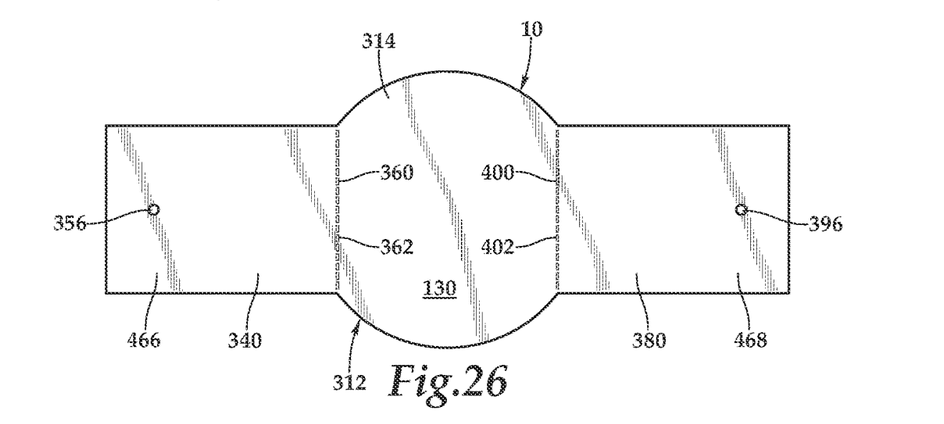
FIG. 26 is a front elevation view of an additional embodiment of a dental medicament applicator.

Referring now to FIG. 24, the retention device 312 of the dental medicament applicator 10 includes the body 314 with the wings 340, 380. The wing 340 has a polygon form 450, which is shown as an isosceles trapezium, which supports the hole 356. Similarly, the wing 380 has a polygon form 452, which is also shown as an isosceles trapezium, which supports the hole 396. Referring now to FIG. 25, the retention device 312 of the dental medicament applicator 10 includes the body 314 with the wings 340, 380. The wing 340 has a double lobe form 454, which supports holes 456, 458. Similarly, the wing 380 has a double lobe form 460, which supports holes 462, 464. Referring now to FIG. 26, the retention device 312 of the dental medicament applicator 10 includes the body 314 with the wings 340, 380. The wing 340 has a rectangular form 466, which supports the hole 356. Similarly, the wing 380 has a rectangular form 468, which supports the hole 396.

Referring now to FIG. 27 through FIG. 32, in some embodiments of the dental medicament applicator 10, a retention device 482 is sized for insertion at a dental site, such as an interproximal site. As shown, the retention device 482 includes a body 484 having a front 486, a rear 488, an upper end 490, a lower end 492, a lateral end 494, and a lateral end 496. The body 484 also includes a vertical axis 498 and a horizontal axis 500.

A wing 510 includes a front 512, a rear 514, an upper end 516, a lower end 518, a proximal end 530, and a distal end 532. The wing 510 has the shape of a lobe 534. Also, the wing 510 has a hole 536 therethrough proximate the distal end 532. The hole 536 may be sized to accept a soft thread or dental floss, for example. The proximal end 530 of the wing 510 is selectively separably coupled to the lateral end 494 by a perforation 540, which provides a visual indicator 542 to assist in the placement of the dental medicament applicator 10. As with other embodiments presented hereinabove, the matrix 130 within the body 484 contains the topical substance. The body 484, in response to being physically affixed to the dental site, delivers the topical substance at a controlled rate to the dental site.

Figures 27, 29, 30, 31:
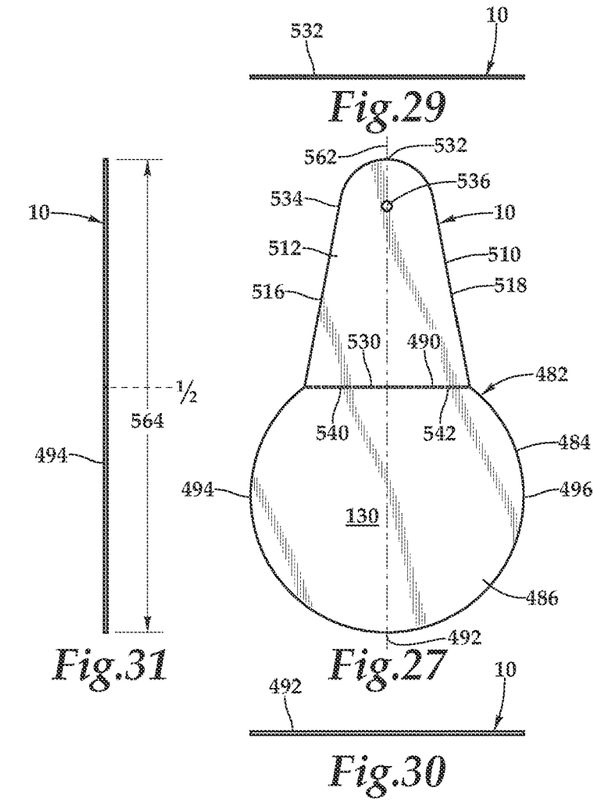
FIG. 27 is a front elevation view of a still further embodiment of a dental medicament applicator.
FIG. 29 is a top plan view of the dental medicament applicator depicted in FIG. 27.
FIG. 30 is a bottom plan view of the dental medicament applicator depicted in FIG. 27.
FIG. 31 is a lateral elevation view of the dental medicament applicator depicted in FIG. 27.
Figure 28:
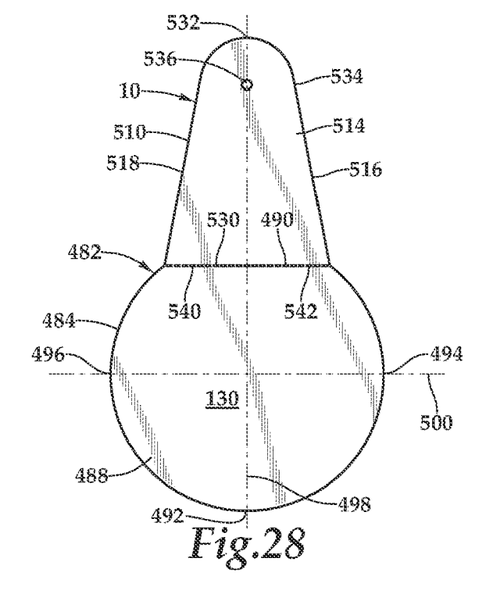
FIG. 28 is a rear elevation view of the dental medicament applicator depicted in FIG. 27.
Figure 32:
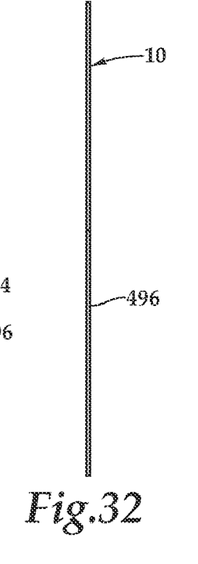
FIG. 32 is another lateral elevation view of the dental medicament applicator depicted in FIG. 27.

In the illustrated embodiment, the retention device 482 includes a transverse axis 562 from the distal end 532 of the wing 510 through the body 484. The transverse axis 562 includes a transverse length 564. The body 484 may extend along the transverse axis 562 and intersect the transverse length 564 from the lateral end 496 to one-half (½) of the transverse length 564 measured from the distal end 532 of the wing 210.

Figures 33, 35:
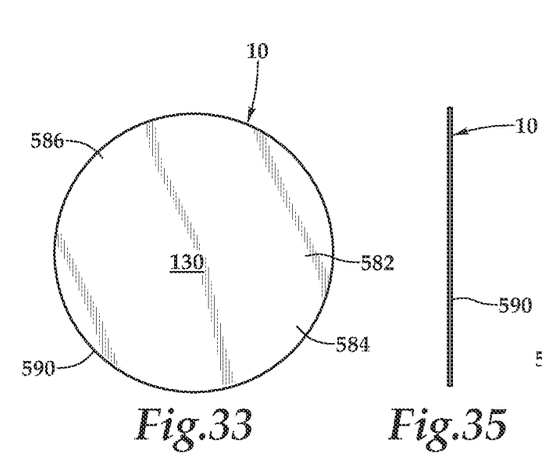
FIG. 33 is a front elevation view of an additional embodiment of a dental medicament applicator.
FIG. 35 is a lateral view of the dental medicament applicator depicted in FIG. 33.
Figure 34:
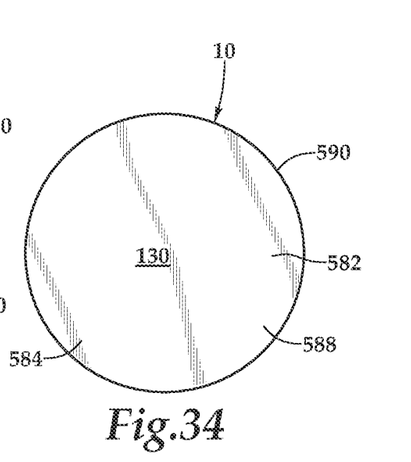
FIG. 34 is a rear elevation view of the dental medicament applicator depicted in FIG. 33.

Referring now to FIG. 33 through FIG. 35, in some embodiments of the dental medicament applicator 10, a retention device 582 is sized for insertion at a dental site, such as an interproximal site. As shown, the retention device 582 includes a body 584 having a front 586, a rear 588, and an outer edge 590. The matrix 130 within the body 584 contains the topical substance. The body 584, in response to being physically affixed to the dental site, delivers the topical substance at a controlled rate to the dental site. The body 584 may include one or more holes for accepting soft thread or dental floss, for example.

Relative terms, such as, but not limited to, "upper," "lower," "front," "rear," "lateral," "vertical," or "horizontal" have been used herein to describe one element's relationship to another element as illustrated in the figures. Such relative terms are intended to encompass different orientations of the device in addition to the orientation depicted in the figures and the use of such relative terms should not be construed as limiting. Further, the order of execution or performance of the methods and techniques illustrated and described herein is not essential, unless otherwise specified. That is, elements of the methods and techniques may be performed in any order, unless otherwise specified, and that the methods may include more or less elements than those disclosed herein. For example, it is contemplated that executing or performing a particular element before, contemporaneously with, or after another element are all possible sequences of execution.

While this invention has been described with reference to illustrative embodiments, this description is not intended to be construed in a limiting sense. Various modifications and combinations of the illustrative embodiments as well as other embodiments of the invention, will be apparent to persons skilled in the art upon reference to the description. It is, therefore, intended that the appended claims encompass any such modifications or embodiments.

What is claimed is:

1. A dental medicament applicator comprising:
    a retention device sized for insertion at a dental site, the dental site being an interproximal site, the retention device including a body having a front, a rear, an upper end, a lower end, a first lateral end, and a second lateral end;
    a first wing having a proximal end and a distal end, the first wing having a hole therethrough proximate the distal end, the first wing being selectively separably coupled to the first lateral end by three points of contact, the three points of contact defining two windows, each of the two windows providing a line-of-sight opening through the retention device;
    a second wing having a proximal end and a distal end, the second wing having a hole therethrough proximate the distal end, the second wing being selectively separably coupled to the second lateral end by three points of contact, the three points of contact defining two windows, each of the two windows providing a line-of-sight opening through the retention device;
    at least one matrix within the body containing a topical substance; and
    the body, in response to being physically affixed to the dental site, delivering the topical substance at a controlled rate to the dental site.

2. The dental medicament applicator as recited in claim 1, wherein each of the respective holes of the first and second wings further comprise holes sized to accept a soft thread.

3. The dental medicament applicator as recited in claim 1, wherein each of the respective holes of the first and second wings further comprise holes sized to accept dental floss.

4. The dental medicament applicator as recited in claim 1, wherein the retention device further comprises:
    a transverse axis from the distal end of the first wing through the body to the distal end of the second wing, the transverse axis having a transverse length; and
    the body extending along the transverse axis and intersecting the transverse length from one-third (⅓) of the transverse length measured from the distal end of the first wing to one-third (⅓) of the transverse length measured from the distal end of the second wing.

5. The dental medicament applicator as recited in claim 1, wherein a surface area of the body is greater than a surface area of each of the first wing and the second wing.

6. The dental medicament applicator as recited in claim 1, wherein a surface area of the body is less than a surface area of the first wing plus the second wing.

7. The dental medicament applicator as recited in claim 1, wherein a surface area of the body is greater than a surface area of the first wing plus the second wing.

8. The dental medicament applicator as recited in claim 1, wherein the matrix further comprises a material selected from the group consisting of biodegradable materials, bioresorbable materials, and resorbable materials.

9. The dental medicament applicator as recited in claim 1, wherein each of the first and second wings comprise a shape selected from the group consisting of single lobes, double lobes, polygon forms, and rectangular forms.

10. The dental medicament applicator as recited in claim 1, wherein the topical substance further comprises a fluoride-containing chemical agent.

11. A dental medicament applicator comprising:
    a retention device sized for insertion at a dental site, the dental site being an interproximal site, the retention device including a body having a front, a rear, an upper end, a lower end, a first lateral end, and a second lateral end;
    a first wing having a proximal end and a distal end, the first wing having a hole therethrough proximate the distal end, the first wing being selectively separably coupled to the first lateral end by three points of contact, the three points of contact defining two windows, each of the two windows providing a line-of-sight opening through the retention device;
    a second wing having a proximal end and a distal end, the second wing having a hole therethrough proximate the distal end, the second wing being selectively separably coupled to the second lateral end by three points of contact, the three points of contact defining two windows, each of the two windows providing a line-of-sight opening through the retention device;
    a transverse axis from the distal end of the first wing through the body to the distal end of the second wing, the transverse axis having a transverse length;
    the body extending along the transverse axis and intersecting the transverse length from one-third (⅓) of the transverse length measured from the distal end of the first wing to one-third (⅓) of the transverse length measured from the distal end of the second wing;

at least one matrix within the body containing a topical substance, the topical substance including a fluoride-containing chemical agent; and the body, in response to being physically affixed to the dental site, delivering the topical substance at a controlled rate to the dental site.

12. A dental medicament applicator comprising:

a retention device sized for insertion at a dental site, the dental site being an interproximal site, the retention device including a body having a front, a rear, an upper end, a lower end, a first lateral end, and a second lateral end;

a first wing having a proximal end and a distal end, the first wing having a hole therethrough proximate the distal end, the first wing being selectively separably coupled to the first lateral end by three points of contact, the three points of contact defining two windows, each of the two windows providing a line-of-sight opening through the retention device;

at least one matrix within the body containing a topical substance; and the body, in response to being physically affixed to the dental site, delivering the topical substance at a controlled rate to the dental site.

13. The dental medicament applicator as recited in claim 12, wherein the hole of the first wing further comprises a hole sized to accept a soft thread.

14. The dental medicament applicator as recited in claim 12, wherein the hole of the first wing further comprises a hole sized to accept dental floss.

15. The dental medicament applicator as recited in claim 12, wherein the retention device further comprises:

a transverse axis from the distal end of the first wing through the body, the transverse axis having a transverse length; and the body extending along the transverse axis and intersecting the transverse length from the second lateral end to one-half (½) of the transverse length measured from the distal end of the first wing.

16. The dental medicament applicator as recited in claim 12, wherein a surface area of the body is greater than a surface area of the first wing.

17. The dental medicament applicator as recited in claim 12, wherein a surface area of the body is greater than twice a surface area of the first wing.

18. The dental medicament applicator as recited in claim 12, wherein the matrix further comprises a material selected from the group consisting of biodegradable materials, bioresorbable materials, and resorbable materials.

19. The dental medicament applicator as recited in claim 12, wherein the first wing comprises a shape selected from the group consisting of single lobes, double lobes, polygon forms, and rectangular forms.

20. The dental medicament applicator as recited in claim 12, wherein the topical substance further comprises a fluoride-containing chemical agent.

* * * * *